US012656282B2

(12) United States Patent
Grodzki et al.

(10) Patent No.: US 12,656,282 B2
(45) Date of Patent: Jun. 16, 2026

(54) MAGNETIC RESONANCE APPARATUS FOR DETECTING AT LEAST ONE PROPERTY OF A SAMPLE

(71) Applicant: Siemens Healthineers AG, Forchheim (DE)

(72) Inventors: David Grodzki, Erlangen (DE); Stephan Biber, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 144 days.

(21) Appl. No.: 18/603,470

(22) Filed: Mar. 13, 2024

(65) Prior Publication Data

US 2024/0310310 A1      Sep. 19, 2024

(30) Foreign Application Priority Data

Mar. 15, 2023    (EP) .................................... 23162073

(51) Int. Cl.
| *G01N 24/08* | (2006.01) |
| *G01N 33/00* | (2006.01) |
| *G01N 35/04* | (2006.01) |

(52) U.S. Cl.
CPC ......... *G01N 24/08* (2013.01); *G01N 33/0098* (2013.01); *G01N 35/04* (2013.01)

(58) Field of Classification Search
CPC ..... G01N 24/08; G01N 33/0098; G01N 35/04
See application file for complete search history.

(56) References Cited

U.S. PATENT DOCUMENTS

| 4,564,812 | A | | 1/1986 | Van Dijk | |
| 5,602,477 | A | * | 2/1997 | McCarthy | .............. G01R 33/44 |
| | | | | | 324/300 |
| 2011/0196228 | A1 | * | 8/2011 | Cho | ..................... G01R 33/481 |
| | | | | | 600/411 |
| 2012/0133358 | A1 | * | 5/2012 | Broz | ................... G01N 24/084 |
| | | | | | 324/318 |
| 2018/0080887 | A1 | * | 3/2018 | Bajema | ................. G01N 33/02 |
| 2018/0238976 | A1 | | 8/2018 | Miljak | |
| 2019/0011383 | A1 | * | 1/2019 | Cohen | ................. G01N 24/085 |
| 2019/0154599 | A1 | * | 5/2019 | Kaminski | .............. G01N 23/18 |

FOREIGN PATENT DOCUMENTS

| CN | 116413648 | A | 7/2023 |
| DE | 202017000763 | U1 | 3/2017 |
| DE | 202017000764 | U1 | 3/2017 |
| DE | 102019220506 | A1 | 6/2021 |
| EP | 0105550 | A1 | 4/1984 |
| JP | H025931 | A | 1/1990 |

* cited by examiner

*Primary Examiner* — Eman A Alkafawi
*Assistant Examiner* — Suresh K Rajaputra
(74) *Attorney, Agent, or Firm* — Banner & Witcoff, Ltd.

(57) ABSTRACT

A magnetic resonance apparatus is described for detecting at least one property of a sample, which may include a foodstuff. The magnetic resonance apparatus comprises a magnet unit, which comprises a base magnet and a RF antenna unit, a sample receiving area at least partially surrounded by the magnet unit, and a transport apparatus for introducing at least one sample into the sample receiving area. The magnetic resonance apparatus comprises an radio frequency (RF) shielding unit, which shields the sample receiving area from the outside, such as a region external to the magnetic resonance apparatus.

16 Claims, 4 Drawing Sheets

FIG 2

MAGNETIC RESONANCE APPARATUS FOR DETECTING AT LEAST ONE PROPERTY OF A SAMPLE

CROSS-REFERENCE TO RELATED APPLICATIONS

The present application claims priority to and the benefit of European Patent Application no. EP 23162073.3, filed Mar. 15, 2023, the contents of which are incorporated herein by reference in their entirety.

TECHNICAL FIELD

The present disclosure relates to a magnetic resonance apparatus and, in particular, to detecting at least one property of a sample, e.g. a foodstuff. The magnetic resonance apparatus comprises a magnet unit, which comprises a base magnet and a radio frequency (RF) unit, and a sample receiving area, that is at least partially supported by the magnet unit, and a transport apparatus for introducing the sample into the sample receiving area.

BACKGROUND

In the quality control of foodstuff, magnetic resonance technology may be used advantageously. For example, meat products may be examined for impurities and/or with regard to their fat content and/or with regard to their quality by means of magnetic resonance technology. The advantage of magnetic resonance technology is that it has no direct contact with the examined object, is non-invasive, and has a good soft tissue contrast.

To use magnetic resonance apparatuses, it is usually necessary for the magnetic resonance apparatus to be arranged within an RF cabin and/or within a special room, as is customary for example in medical magnetic resonance apparatuses. However, such RF shielded rooms and/or cabins are complex and expensive.

SUMMARY

The object of the present disclosure is to provide a magnetic resonance apparatus that may be used outside an RF shielded room. The object is achieved by the embodiments as described herein, including the claims.

The disclosure is based on a magnetic resonance apparatus for detecting at least one property of a sample, e.g. a foodstuff, comprising a magnet unit, which comprises a base magnet and a RF antenna unit, a sample receiving area, the sample receiving area being at least partially surrounded by the magnet unit, and a transport apparatus for introducing the sample into the sample receiving area. According to the disclosure, the magnetic resonance apparatus has a RF shielding unit that shields the sample receiving area from the outside.

The magnetic resonance apparatus may e.g. comprise a non-medical and/or non-diagnostic magnetic resonance apparatus. The magnetic resonance apparatus may e.g. be designed to detect magnetic resonance data and/or image data, it being possible to determine at least one property of the samples inside the sample receiving area, e.g. of foodstuffs. For example, a quality of meat products and/or impurities of meat products and/or a fat content of meat products can be detected and/or determined in this way.

The magnet unit may e.g. have a base magnet, such as a cylindrical base magnet. The base magnet is configured to generate a homogeneous base magnetic field with a defined magnetic field strength, such as, for example, with a magnetic field strength of 0.55 T or 1.5 T or 3 T, etc. The base magnet is configured to generate a strong, constant and homogeneous base magnetic field. The homogeneous base magnetic field may e.g. be arranged and/or found within the sample receiving area of the magnetic resonance apparatus. Furthermore, the magnet unit comprises the RF antenna unit. The RF antenna unit is configured to emit RF pulses and to acquire magnetic resonance data. The RF antenna unit may likewise be cylindrical in design and arranged within a cavity enclosed by the cylindrical base magnet.

In addition, the magnetic resonance apparatus may also comprise a gradient system which is configured to generate magnetic field gradients used for spatial encoding during imaging. Such a gradient system may also be cylindrical and arranged within the cavity enclosed by the cylindrical base magnet.

The magnet unit also comprises a central cylindrical recess that comprises the sample receiving area. The sample receiving area is cylindrically surrounded by the magnet unit, e.g. by the base magnet, the RF antenna unit and, if present, by the gradient system. On a front side of the magnet unit, the sample receiving area has an inlet opening. On a rear side of the magnet unit, the sample receiving area may e.g. have an outlet opening. The inlet opening is configured to introduce samples into the sample receiving area. The outlet opening, on the other hand, is configured to remove samples from the sample receiving area, for example, after completion of the magnetic resonance measurement of the sample. Alternatively, the sample receiving area may have only one opening which has a function of the inlet opening and the outlet opening.

A Field of View (FOV) and/or an isocenter of the magnetic resonance apparatus may e.g. arranged within the sample receiving area. The FOV may comprise a detection range of the magnetic resonance apparatus within which the conditions for detection of magnetic resonance data are present, such as, for example, a homogeneous base magnetic field. The isocenter of the magnetic resonance apparatus may comprise the area and/or point within the magnetic resonance apparatus that has the optimal and/or ideal conditions for acquiring magnetic resonance data. For instance, the isocenter may comprise the most homogeneous magnetic field area within the magnetic resonance apparatus.

The transport apparatus is configured to introduce samples into the sample receiving area. For instance, the transport apparatus is configured for the ongoing and/or continuous introduction of samples into the sample receiving area. Furthermore, after the magnetic resonance measurement of the sample, the transport apparatus is also configured to bring the sample out of the sample receiving area. In this case, the transport apparatus may e.g. comprise a conveyor belt with a direction of transport, the conveyor belt introducing samples into the sample receiving area via the inlet opening in the direction of transport and removing samples from the patient receiving area via the outlet opening. In this case, a plurality of samples can be positioned and/or stored on the conveyor belt at the same time, the individual samples e.g. being at a defined distance from one another. For example, the defined distance between the individual samples can be dimensioned in such a way that only a single sample is arranged within the FOV during a magnetic resonance measurement.

The magnetic resonance apparatus comprises the RF shielding unit for shielding from RF radiation. The RF shielding unit shields the sample receiving area from the outside (i.e. a region external to the magnetic resonance apparatus) with regard to RF radiation. In this case, individual components of the RF shielding unit may e.g. have electrical contact with one another so that the interior of the sample receiving area is shielded from the outside. For example, shielding and/or attenuation of 40 dB to 100 dB can be achieved in the range of the Larmor frequency by means of the RF shielding unit. In addition, the electrical contact of the RF shielding unit can also be connected to a metal housing of the magnet unit.

The present disclosure has the advantage that simple and cost-effective RF shielding can be provided, which is already covered by the magnetic resonance apparatus. Thus, it is possible to dispense with an additional RF cabin and/or an additional shielded room within which the magnetic resonance apparatus is arranged. This also enables the simple installation of a magnetic resonance apparatus according to the disclosure, even in a non-RF shielded environment.

A further advantage of the disclosure is that it is possible to provide a simple and radiation-free detection of sample properties, e.g. of properties of foodstuffs, for example for quality control of foodstuffs. In addition, the detection of sample properties of foodstuffs for example may be carried out in a contactless manner with the sample, so that detection, for example in the case of quality control, is also associated with less cleaning effort and/or can be simplified in compliance with hygiene regulations. In addition, data with a high soft tissue contrast can also be provided by means of magnetic resonance imaging, so that properties such as, for example, a fat content and/or a quality in meat products can be advantageously ascertained.

In an advantageous development of the magnetic resonance apparatus according to the disclosure, it can be provided that the sample receiving area is surrounded cylindrically by the magnet unit, has an inlet opening and an outlet opening, the RF shielding unit being arranged around the inlet opening and/or around the outlet opening. In an embodiment, the inlet opening of the patient receiving area is arranged on a front side of the magnet unit and the outlet opening of the patient receiving area is arranged on a rear side of the magnet unit. Advantageous RF shielding of the sample receiving area can be achieved through the arrangement of the RF shielding unit. For instance, is it possible to prevent such undesirable impairments, for example the detection of a sample property by means of the magnetic resonance apparatus or even impairment of devices located outside the magnetic resonance apparatus.

In an advantageous development of the magnetic resonance apparatus according to the disclosure, it can be provided that the RF shielding unit is arranged outside the sample receiving area. This embodiment of the disclosure has the advantage that the sample receiving area is not restricted by the RF shielding unit and a large sample receiving area can be maintained for magnetic resonance measurements of samples. In addition, an arrangement and/or a positioning of the RF shielding unit can be arranged in a structurally simple manner on the front side and/or on the rear side of the magnet unit and does not cause any interferences within the sample receiving area and/or during a magnetic resonance measurement.

In an advantageous development of the magnetic resonance apparatus according to the disclosure, it can be provided that the RF shielding unit has at least one door unit, the sample receiving area being configured to be closable or openable by means of the at least one door unit. In an embodiment, the at least one door unit comprises at least one door and/or one flap, the at least one door and/or the at least one flap also being configured as an RF shielding element. In this case, the at least one door and/or the at least one flap may be configured, for example, to be electrically conductive or may have an electrical contact with a housing of the magnet unit, for example in an embodiment of the at least one door and/or the at least one flap made of a metal. In an embodiment, the sample receiving area may be opened by means of the at least one door unit for introducing a sample into the sample receiving area and/or for removing a sample from the sample receiving area. On the other hand, during a magnetic resonance measurement the sample receiving area is closed, e.g. closed RF-tight (i.e. RF-sealed), by means of the at least one door unit. The magnet unit may e.g. have two door units, a first door unit being arranged before the inlet opening of the sample receiving area and a second door unit being arranged after the outlet opening of the sample receiving area. Alternatively, the RF shielding unit may also comprise only a single door unit, the inlet opening in such an embodiment also having the function of an outlet opening, and the sample receiving area on the rear side being designed to be tightly closed, e.g. closed in an RF-tight manner.

This embodiment of the disclosure has the advantage that simple RF shielding can be achieved during a magnetic resonance measurement and at the same time, good accessibility to the sample receiving area is maintained between the individual magnetic resonance measurements.

In an advantageous development of the magnetic resonance apparatus according to the disclosure, it can be provided that the RF shielding unit has at least one cylindrical spacing element that is arranged on a front side and/or on a rear side of the magnet unit, the at least one spacing element being arranged between the sample receiving area and the at least one door unit. In an embodiment, the at least one cylindrical spacing element is configured as an RF shielding element, for example, as a metal cylinder. The cylindrical spacing element may be only a few centimeters (cm) long. In addition, the cylindrical spacing element may also be up to 200 cm or more in length and can therefore be adapted to different space requirements. In an embodiment, the at least one cylindrical spacing element is arranged on a housing of the magnet unit, e.g. a front side and/or a rear side of the magnet unit. This embodiment of the disclosure has the advantage that the at least one door unit can be arranged in an area with a low alternating field and thus undesirable interferences of the magnetic field and/or undesirable eddy currents can be prevented.

In an advantageous development of the magnetic resonance apparatus according to the disclosure, it can be provided that at least one cylindrical spacing element is arranged in an RF-tight (i.e. RF-scaled) manner on the front side and/or on the rear side of the magnet unit. For the RF-tight arrangement of the at least one cylindrical spacing element, the at least one cylindrical spacing element can be welded to a housing of the magnet unit, e.g. to a front housing side and/or to a rear housing side of the magnet unit. Furthermore, the at least one cylindrical spacing element may also be clamped to the housing of the magnet unit, e.g. to a front housing side and/or to a rear housing side of the magnet unit. For an RF-tight arrangement of the at least one cylindrical spacing element, for example, RF-tight contact springs can be arranged between the at least one cylindrical spacing element and the housing unit of the magnet unit, e.g. the front housing side and/or the rear housing side of the magnet unit. Such contact springs may e.g. be made of metal and/or be electrically conductive in design, so that an electrical contact between the housing unit of the magnet unit, e.g. the front housing side and/or the rear housing side of the magnet unit and the at least one cylindrical spacing element is available for RF shielding. For example, these contact springs, e.g. the electrically conductive contact springs, may have a lamellar structure. In this way, RF shielding may be achieved and/or maintained particularly easily and cost-effectively by the arrangement of the cylindrical spacing element.

In an advantageous development of the magnetic resonance apparatus according to the disclosure, it can be provided that the at least one door unit has at least one flap and the RF shielding unit has at least one electric drive unit and/or at least one pneumatic drive unit, it being possible for a drive torque for a movement of the at least one flap of the at least one door unit to be generated by means of the at least one electric drive unit and/or the at least one pneumatic drive unit. The at least one flap of the at least one door unit is configured to open or close the sample receiving area. The at least one flap may e.g. be arranged on one side of the at least one cylindrical spacing element facing away from the magnet unit. The at least one flap can perform a linear movement or a rotary movement to open the sample receiving area and/or to close the sample receiving area.

In an embodiment, the at least one electric drive unit and/or the at least one pneumatic drive unit are arranged outside the sample receiving area and outside the area enclosed and/or enclosable by the RF shielding unit. The at least one electric drive unit can have an electric motor. In this way, a simple and cost-effective drive unit can be provided for opening and/or closing the at least one door unit. In addition, an undesirable interference and/or interaction with the RF field of the magnet unit can be prevented by means of the pneumatic drive unit. In addition, by means of at least one cylindrical spacing element, the drive unit, e.g. the electric drive unit and/or the pneumatic drive unit, are arranged at a distance from the magnet unit and are thus arranged in an area with a low magnetic field and/or a low RF field.

In an advantageous development of the magnetic resonance apparatus according to the disclosure, it can be provided that the RF shielding unit has at least one transmission element configured to transmit a drive torque generated by the at least one electric drive unit and/or the at least one pneumatic drive unit to the at least one flap of the at least one door unit. If the RF shielding unit comprises an electric drive unit, the at least one transmission element may e.g. be formed by a transmission belt and/or a chain. On the other hand, if the RF shielding unit comprises a pneumatic drive unit, the at least one transmission element comprises, for example, an air hose and/or a pneumatic line. In this way, the drive unit, e.g. the electric drive unit and/or the pneumatic drive unit, may be advantageously arranged at a great distance from the magnet unit, e.g. from the sample receiving area of the magnet unit, for example, a distance of up to 3 meters (m) from the magnet unit. Thus, undesirable interactions and/or impairments between the drive unit, e.g. the electric drive unit, and the RF field of the magnet unit can be advantageously prevented. In particular, the electric drive unit can thus be protected from undesirable interference and/or impairment of its functionality.

In an advantageous development of the magnetic resonance apparatus according to the disclosure, it can be provided that the at least one door unit comprises a first flap and a second flap, it being possible to close the first flap and the second flap in an RF-tight manner. Thus, a simple opening and closing of the sample receiving area can be achieved. In addition, in this way the individual flap can be made smaller, whereby a weight bearing down on the closing mechanism can be reduced and wear thus reduced.

In an advantageous development of the magnetic resonance apparatus according to the disclosure, it can be provided that the at least one door unit has at least one RF seal, the RF seal being arranged in a contact area between the first flap and the second flap and/or in a contact area between the first flap and the at least one cylindrical spacing element and/or in a contact area between the second flap and the at least one cylindrical spacing element. In an embodiment, the at least one door unit has a plurality of RF seals which are arranged in all the contact areas of the first flap with the second flap and in all the contact areas of the first flap and the second flap with the at least one cylindrical spacing element. The individual RF seals may e.g. be formed by RF-tight contact springs. In an embodiment, such RF-tight contact springs are made of metal and/or are electrically conductive in design, so that in a closed state of the at least one door unit there is an electrical contact between the two flaps and/or between the first flap and the at least one cylindrical spacing element and/or the second flap and the at least one cylindrical spacing element. For example, these contact springs, e.g. the electrically conductive contact springs, may have a lamellar structure. In this way, effective RF shielding between all moving components and/or on all contact surfaces of the moving components of the at least one door unit can be achieved in a particularly simple and cost-effective manner.

In an advantageous development of the magnetic resonance apparatus according to the disclosure, it can be provided that the transport apparatus has at least one conveyor belt, the at least one conveyor belt having at least one recess, the first flap and/or the second flap being arranged at least partially within the at least one recess in a closed state of the at least one door unit. The at least one recess may have a longitudinal extension that is aligned parallel to a transverse direction of the conveyor belt. The at least one conveyor belt may e.g. have a plurality of recesses, which are arranged one after the other in a transverse direction of the conveyor belt. The closed state of the at least one door unit may e.g. comprise a closing of the two flaps, so that each of these two flaps has contact with the other of the two flaps. The contact between the two flaps of the at least one door unit can comprise a mechanical and, particularly advantageously, also an electrical contact between the first flap and the second flap. In an embodiment, a contact area of the first flap with the second flap and/or a contact area of the second flap with the first flap is arranged within the at least one recess in a closed state of the at least one door unit. In this way, the first flap together with the second flap can establish contact, e.g. electrical contact, with one another through the at least one recess in the conveyor belt when the two flaps are closed, and thus generate RF shielding in this closed state of the at least one door unit.

In an advantageous development of the magnetic resonance apparatus according to the disclosure, it can be provided that the at least one conveyor belt has a plurality of recesses that are arranged in a line one after the other in a transverse direction of the conveyor belt, the first flap having a tooth system in a contact area with the second flap and the second flap having a tooth system corresponding to the first flap in a contact area with the first flap, the two tooth systems interlocking through the recesses of the conveyor belt. In an embodiment, the recesses extending in the transverse direction of the conveyor belt, e.g. a shape and/or contour of the recesses, are adapted to the tooth system of the first flap and to the tooth system of the second flap and/or are configured to correspond to the tooth system of the first flap and the second flap. The transverse direction of the conveyor belt may e.g. extend transversely to the running direction and/or the direction of transport of the conveyor belt. Due to the plurality of recesses in the transverse direction of the conveyor belt, an advantageous interlocking of the two flaps can be ensured on the one hand and, on the other hand, a stability of the conveyor belt can also be maintained.

In an advantageous development of the magnetic resonance apparatus according to the disclosure, it can be provided that the at least one conveyor belt has a plurality of recesses arranged one after the other in the longitudinal direction. The longitudinal direction of the at least one conveyor belt may e.g. extend in the direction of transport and/or direction of movement of the conveyor belt. The recesses may e.g. be arranged at uniform intervals one after the other in the longitudinal direction on the conveyor belt. In this case, a distance between the individual recesses in the longitudinal direction can also be adapted to the samples to be examined. For example, a storage area for storage and/or positioning of a sample can be arranged between two recesses arranged in the longitudinal direction. This embodiment of the disclosure has the advantage that a high level of efficiency can be achieved when introducing the samples, for example, foodstuffs, into the sample receiving area. For example, the samples can be positioned at a short distance from one another on the conveyor belt and the at least one door unit may still be closed in an RF-tight manner during each magnetic resonance measurement of a sample.

In an advantageous development of the magnetic resonance apparatus according to the disclosure, it can be provided that the transport apparatus has at least two conveyor belts, which are arranged one after the other in the direction of transport, and at least one transition area between the two conveyor belts, in this at least one transition area the at least one door unit being arranged in a closed state of the at least one door unit. For example, the transport apparatus may comprise three conveyor belts, which include a first conveyor belt being arranged within the sample receiving area and within the area enclosed by the RF shielding unit. On the other hand, a second and a third conveyor belt are located outside the area enclosed by the RF shielding unit and are arranged in the direction of transport before the magnet unit or after the magnet unit, respectively. The transition area may e.g. have a length in the direction of transport which enables a closing of the door unit, e.g. the two flaps of the door unit, and also ensure a sample transfer between the two conveyor belts in the open state of the door unit. This embodiment of the disclosure enables simple and reliable closing of the at least one door unit. For instance, reliable RF shielding during a magnetic resonance measurement can be achieved in this way.

In an advantageous development of the magnetic resonance apparatus according to the disclosure, it can be provided that the transport apparatus has at least one conveyor belt, the at least one conveyor belt comprising an RF shielding material. In this case, the at least one conveyor belt may e.g. comprise RF shielding segments. In an embodiment, the conveyor belt, which is arranged outside the sample receiving area, comprises the RF shielding material and/or the RF shielding segments. The RF shielding material may e.g. comprise an electrically conductive material, e.g. a metal. On the other hand, the partial area of the transport apparatus, e.g. the conveyor belt arranged within the sample receiving area, may be made of a non-conductive material to prevent unwanted attraction by the base magnet of the magnet unit and/or the generation of eddy currents. When closing the at least one door unit, e.g. the two flaps of the at least one door unit, the RF shielding material may produce the effect of the two flaps of the at least one door unit being able to come into contact with one another, e.g. into electrical contact with one another, and in doing so produce a closed RF shielding.

In an advantageous development of the magnetic resonance apparatus according to the disclosure, it can be provided that the magnetic resonance apparatus has a control unit, the control unit being configured to automatically adapt a movement of the transport apparatus and/or a closing of the at least one door unit to magnetic resonance measurements of successive samples. In this way, a time-saving and automated and/or automatic detection of sample properties can be advantageously provided.

The control unit according to the disclosure comprises at least one computing module and/or a processor. The control unit may be configured to execute computer-readable instructions. For example, the control unit may comprise a storage unit, computer-readable information being stored on the storage unit, and the control unit being configured to load the computer-readable information from the storage unit and to execute the computer-readable information. In this way, the control unit according to the disclosure is configured to automatically adapt a movement of the transport apparatus and/or a closing of the at least one door unit to magnetic resonance measurements of successive samples.

The components of the control unit may for the most part be configured in the form of software components. In principle, however, these components can also be realized in part in the form of software-supported hardware components, for example FPGAs or the like, e.g. when it comes to particularly fast calculations. Likewise, the required interfaces can be designed as software interfaces, for example, if it is only a matter of transferring data from other software components. However, they can also be designed as hardware-based interfaces which are controlled by suitable software. Of course, it is also conceivable that a plurality of the aforementioned components are combined in the form of a single software component or software-supported hardware component.

BRIEF DESCRIPTION OF THE DRAWINGS

Further advantages, features and details of the disclosure will emerge from the exemplary embodiments described hereinafter, and with reference to the drawings, in which:

FIG. 2 illustrates a top view of a conveyor belt of an example magnetic resonance apparatus;

DETAILED DESCRIPTION OF THE DISCLOSURE

Figure 1:
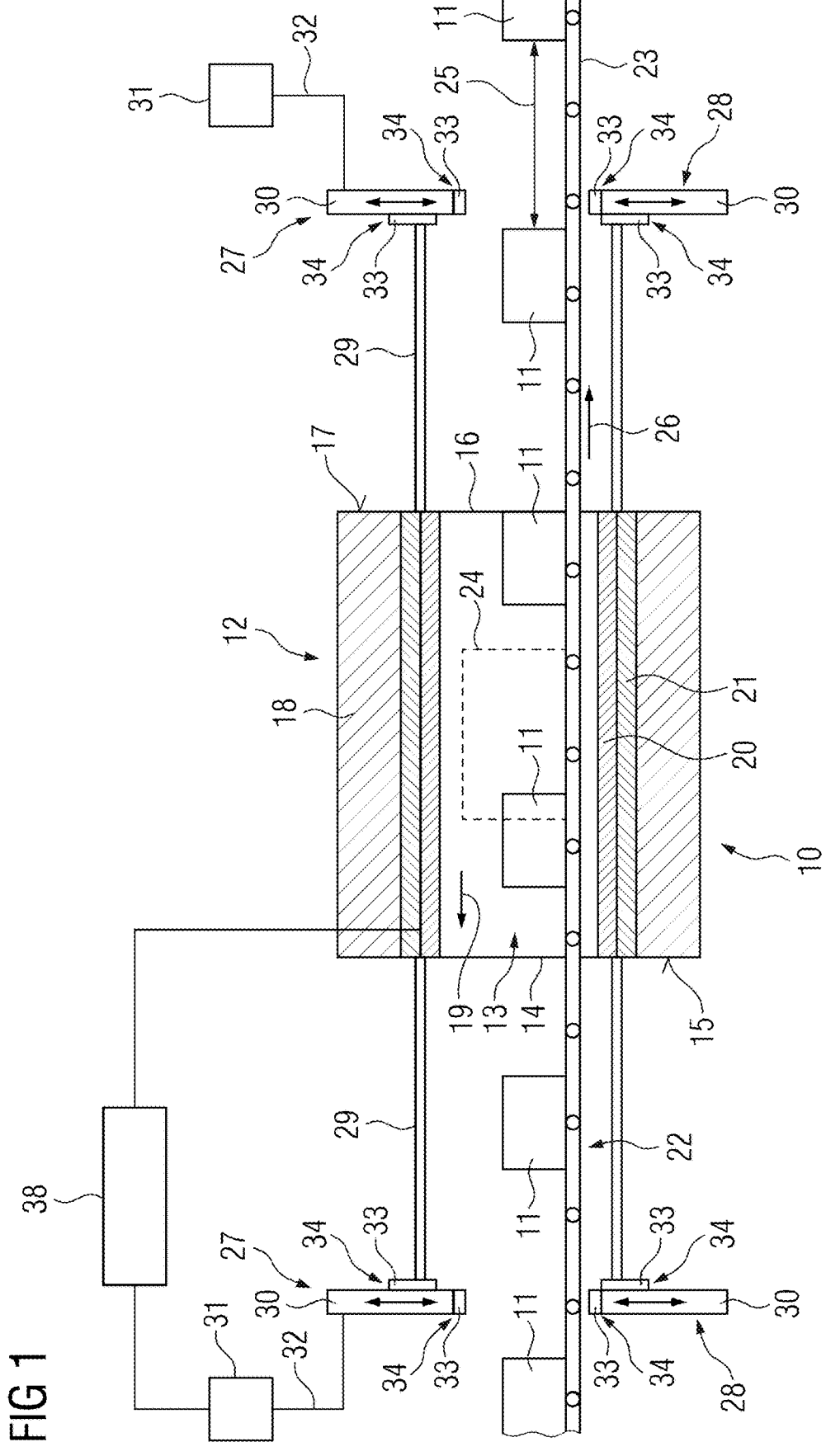
FIG. 1 illustrates a first embodiment of an example magnetic resonance apparatus with RF shielding in a diagrammatic view.

FIG. 1 shows a diagrammatic view of a first exemplary embodiment of a magnetic resonance apparatus 10. The magnetic resonance apparatus 10 is configured, e.g. to detect at least one property of a sample 11, which may comprise a foodstuff for instance. For example, a quality of meat products and/or a fat content of meat products and/or unwanted inclusions in meat products is determined and/or detected by means of the magnetic resonance apparatus 10 according to the disclosure.

The magnetic resonance apparatus 10 comprises a magnet unit 12 and a sample receiving area 13. The sample receiving area 13 extends cylindrically through the magnet unit 12 so that the magnet unit 12 surrounds the sample receiving area 13 cylindrically. The sample receiving area 13 also has an inlet opening 14, which is arranged on a front side 15 of the magnet unit 10, and an outlet opening 16, which is arranged on a rear side 17 of the magnet unit 12. In principle, however, an embodiment of the sample receiving area 13 deviating therefrom is conceivable, such as, for example, a sample receiving area 13 with only one opening that has the function of an inlet opening and an outlet opening at the same time.

The magnet unit 12 has a superconducting base magnet 18, which is configured to generate a homogeneous base magnetic field 19. Furthermore, the magnet unit 12 has a RF antenna unit 20, which is configured to emit RF pulses and to detect magnetic resonance (MR) signals. Due to the RF pulses irradiated into the sample receiving area 13, which are irradiated by the RF antenna unit 20, magnetic resonance signals are produced in the individual samples, which are in turn received by means of the RF antenna unit 20. The RF antenna unit 20 has a transmit mode and a receive mode for this purpose. In the present exemplary embodiment, the magnet unit 12 also has a gradient coil unit 21, which is used to generate magnetic field gradients that are used for spatial encoding during a magnetic resonance measurement.

The magnetic resonance apparatus 10 has a transport apparatus 22 for introducing samples 11 and/or objects into the sample receiving area 13. In the present exemplary embodiment, the transport apparatus 22 comprises a single conveyor belt 23 on which the individual samples 11 are introduced into the sample receiving area 13, e.g. into an FOV 24 and/or an isocenter of the magnet unit 12 for magnetic resonance measurement. In the present exemplary embodiment, the individual samples 11 are at a defined distance 25 from one another on the conveyor belt 23, so that only one sample 11 at a time for a magnetic resonance measurement is located within the FOV 24 and/or in the isocenter of the magnet unit 12. The conveyor belt 23 has a direction of transport 26, which extends in the longitudinal extension of the conveyor belt 23. In addition, the conveyor belt 23 has a substantially longer extension than the sample receiving area 13, so that the individual samples 11 are continuously introduced from the outside one after the other into the sample receiving area 13, remain there briefly in the FOV 24 and/or in the isocenter of the magnet unit 12 for magnetic resonance measurement, and then leave the sample receiving area 13 again in the direction of transport 26 via the outlet opening 16.

The magnetic resonance apparatus 10 also has a RF shielding unit 27, which shields the sample receiving area 13 from the outside (i.e. a region external to the magnetic resonance apparatus 10). The RF shielding unit 27 is arranged outside the sample receiving area 13. In the present exemplary embodiment, the RF shielding unit 27 is arranged both around the inlet opening 14 of the sample receiving area 13 and around the outlet opening 16 of the sample receiving area 13.

For RF shielding of the sample receiving areas 13, the RF shielding unit 27 has two door units 28. A first door unit 28 is arranged in an area facing a front side 15 of the magnet unit 12. A second door unit 28 is arranged in an area facing a rear side 17 of the magnet unit 12. However, the two door units 28 are arranged at a distance from the magnet unit 12. For this purpose, the RF shielding unit 27 has two cylindrical spacing elements 29, which are arranged between the magnet unit 12, e.g. the sample receiving area 13, and the two door units 28. A first cylindrical spacing element 29 is arranged on the front side 15 of the magnet unit 12 and a second cylindrical spacing element 29 is arranged on the rear side 17 of the magnet unit 12. In addition, the two door units 27 are each arranged on a side of the cylindrical spacing elements 29 facing away from the magnet unit 12. The two cylindrical spacing elements 29 may be of any suitable length. For example, the two cylindrical spacing elements 29 may be only a few cm long or up to 200 cm long. Some example ranges of the two cylindrical spacing elements 29 include between 100 cm and 200 cm long, between 120 cm and 200 cm long, between 140 cm and 200 cm long, between 160 cm and 200 cm long, between 180 cm and 200 cm long, etc.

The first cylindrical spacing element 29 is arranged around the inlet opening 14 on the front side 15 of the magnet unit 12. In an embodiment, the first cylindrical spacing element 29 is arranged on a front housing of the magnet unit 12. In the present exemplary embodiment, the first cylindrical spacing element 29 is welded to the front side 15 and/or the front housing of the magnet unit 12. Alternatively, the first cylindrical spacing element 29 can also be clamped to the front side 15 and/or the front housing of the magnet unit 12, and a contact area between the first cylindrical spacing element 29 and the front side 15 and/or the front housing of the magnet unit 12 can be kept RF-tight by means of RF-tight contact springs.

The second cylindrical spacing element 29 is arranged around the outlet opening 16 on the rear side 17 of the magnet unit 12. In an embodiment, the second cylindrical spacing element 29 is arranged on a rear housing of the magnet unit 12. In the present exemplary embodiment, the second cylindrical spacing element 29 is welded to the rear side 17 and/or to the rear housing of the magnet unit 12. Alternatively, the second cylindrical spacing element 29 can also be clamped to the rear side 17 and/or the rear housing of the magnet unit 12, and a contact area between the second cylindrical spacing element 29 and the rear side 17 and/or the rear housing of the magnet unit 12 can be kept RF-tight by means of RF-tight contact springs.

The two door units 28 are configured to open or close the sample receiving area 13. The two door units 28 each have two flaps 30 and one drive unit 31. In the present exemplary embodiment, the drive units 31 are each formed by an electric drive unit by means of which a drive torque for a closing movement and/or opening movement of the two flaps 30 of the door units 28 is generated. In addition, the two door units 28 each have a transmission element 32 configured to transmit the drive torque generated by the electric drive unit to the two flaps 30. The transmission element 32 comprises a transmission belt and/or a chain. In an alternative embodiment, the two drive units 31 can each be configured as pneumatic drive units with a pneumatic transmission element, for example an air hose.

The first flaps 30 and the second flaps 30 are configured such that they can be closed in an RF-tight manner. For this purpose, the two door units 28 each have a plurality of RF seals 33. These RF seals 33 are each arranged in contact areas 34 between the first flaps 30 and the second flaps 30. In addition, at least one RF seal 33 is arranged in a contact area 34 between the first flaps 30 and the cylindrical spacing elements 29. In addition, at least one RF seal 33 is arranged in a contact area 34 between the second flaps 30 and the cylindrical spacing elements 29. The RF seals may e.g. be configured as contact springs, e.g. as electrically-conductive contact springs. The RF-tight contact springs may e.g. be electrically conductive so that there is an electrical contact between the two flaps 30 and/or between the first flaps 30 and the cylindrical spacing elements 29 and/or the second flaps and the cylindrical spacing elements 29 for RF shielding.

Figure 2:
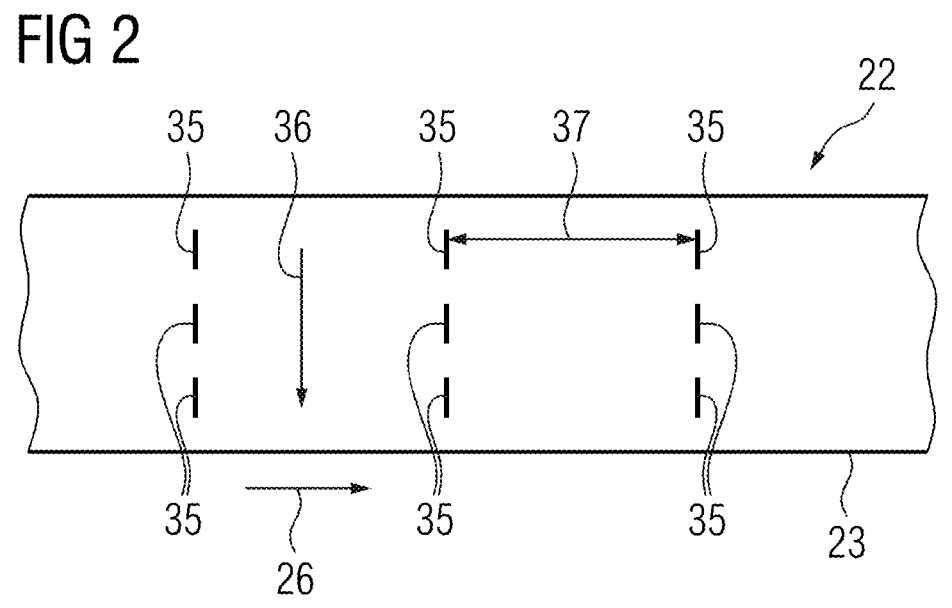

For RF-tight closing of the first flaps 30 with the second flaps 30, the conveyor belt 23 of the transport apparatus 22 has recesses 35 (FIG. 2). The recesses 35 extend at uniform intervals in the transverse direction 36 of the conveyor belt 23, the transverse direction 36 being oriented essentially transversely to the longitudinal direction of the conveyor belt 23 and/or transversely to the direction of transport 26 of the conveyor belt 23. In an embodiment, the recesses 35 are arranged one after the other in a line in the transverse direction 36. In addition, each of the first flaps 30 also has a tooth system, which is configured to correspond to the recesses 35 of the conveyor belt 23 in the transverse direction 36. Moreover, the second flaps 30 also have a tooth system, which is configured to correspond to the tooth system of the first flaps 30.

In a closed state of the respective door unit 28, the first flaps 30 and/or the second flaps 30 are at least partially arranged inside the recesses 35 of the conveyor belt 23. In this case, the tooth systems of the first flaps 30 engage with the tooth systems of the second flaps 30. In the closed state of the two door units 28, a contact, e.g. a mechanical contact and an electrically conductive contact, is established between the two flaps 30. A contact area 34 is arranged between the two flaps 30 in the recesses 35 of the conveyor belt 23. An RF-tight closing of the door units 28 is achieved by means of the electrically-conductive contact between the two flaps 30.

Furthermore, the conveyor belt 23 has a plurality of recesses 35 arranged one after the other in the longitudinal direction and/or the direction of transport 26 (FIG. 2). In this case, the recesses 35, which are arranged one after the other in the longitudinal direction and/or the direction of transport 26, are arranged at uniform intervals 37 to one another on the conveyor belt 23. In an embodiment, storage areas for storing the samples 11 are arranged between the recesses 35 in the longitudinal direction and/or in the direction of transport 26, respectively. In the case of the recesses 35 arranged one after the other in the longitudinal direction and/or in the direction of transport 26, the pattern of the recesses 35 in a transverse direction 36 of the conveyor belt 23 repeats itself, so that after each sample 11 it is possible to close the door units 28.

Furthermore, the magnetic resonance apparatus 10 has a control unit 38 (FIG. 1). By means of the control unit 38, the magnetic resonance apparatus 10 is centrally controlled. For example, by means of the control unit 38, a RF pulse is controlled by means of the RF antenna unit 20. In addition, the recording of magnetic resonance data and/or the evaluation of the recorded magnetic resonance data is also controlled by means of the control unit 38. For this purpose, the control unit may include units such as, for example, evaluation units, etc.

Furthermore, the control unit 38 is configured to automatically adapt a movement of the transport apparatus 22, e.g. of the conveyor belt 23, and/or a closing of the second door units 28 to magnetic resonance measurements of successive samples 11. After a magnetic resonance measurement, the two door units 28 are controlled by the control unit 38 in such a way that they open the flaps 30. After the flaps 30 are opened, the transport apparatus 22 is controlled in such a way that the conveyor belt 23 proceeds until the next sample 11 is arranged in the FOV 24 of the magnet unit 12. Subsequently, the two door units 28 are controlled by the control unit 38 in such a way that they close the flaps 30 again. Subsequently, the magnetic resonance measurement of the sample 11 is carried out, controlled by the control unit 38.

Figure 3:
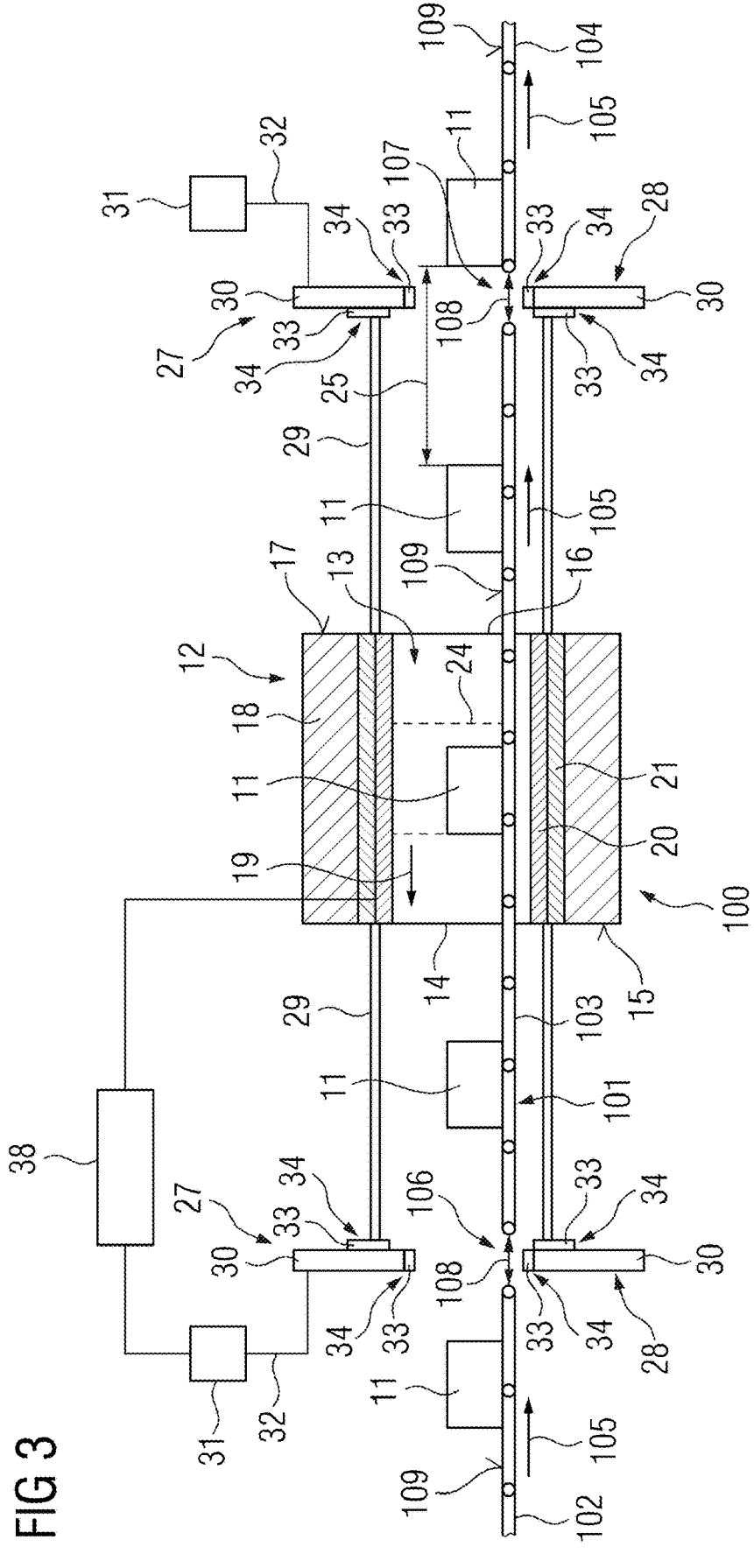
FIG. 3 illustrates a second embodiment of the example magnetic resonance apparatus with RF shielding in a diagrammatic view.

FIG. 3 shows an alternative exemplary embodiment of a magnetic resonance apparatus 100. Essentially uniform components, features, and functions are denoted by the same reference characters among FIGS. 1-4. The following description is essentially limited to the differences to the exemplary embodiment in FIGS. 1 and 2, reference being made to the description of the exemplary embodiment in FIGS. 1 and 2 with regard to components, features, and functions remaining the same.

The magnetic resonance apparatus 100 in FIG. 3 differs from the magnetic resonance apparatus 10 in FIG. 1 in an embodiment of the transport apparatus 101. The transport apparatus 101 has three conveyor belts 102, 103, 104, which are arranged one after the other in the direction of transport 105. A first conveyor belt 102 extends in the direction of transport 105 as far as the first door unit 28. A second conveyor belt 103 extends in the direction of transport 105 from the first door unit 28 as far as the second door unit 28. A third conveyor belt 104 extends in the direction of transport 105 away from the second door unit 28. In each case, two adjacent conveyor belts 102, 103, 104 have a transition area 106, 107. In particular, a first transition area 106 is arranged between the first conveyor belt 102 and the second conveyor belt 103, and a second transition area 107 is arranged between the second conveyor belt 103 and the third conveyor belt 104.

In the direction of transport 105, the two transition areas 106, 107 have a length 108, which essentially corresponds to a thickness of the door units 28. The first door unit 28 is arranged in the first transition area 106, and the second door unit 28 is arranged in the second transition area 107. In a closed state of the first door unit 28, the first flap 30 and the second flap 30 of the first door unit 28 are thus located in the first transition area 106 and/or between the first conveyor belt 102 and the second conveyor belt 103. Likewise, in a closed state of the second door unit 28, the first flap 30 and the second flap 30 of the second door unit 28 are thus located in the second transition area 107 and/or between the second conveyor belt 103 and the third conveyor belt 104. The individual conveyor belts 102, 103, 104 also have a continuous storage area 109 for storage of samples 11, the storage area 109 being free of recesses.

An embodiment and arrangement of the magnet unit 12 corresponds to the embodiments relating to FIG. 1, to which reference is hereby made. An embodiment and arrangement of the cylindrical spacing elements 29 corresponds to the embodiments relating to FIG. 1, to which reference is also hereby made. In addition, an embodiment and arrangement of the door units 28 also corresponds to the embodiments relating to FIG. 1, to which reference is hereby made.

Figure 4:
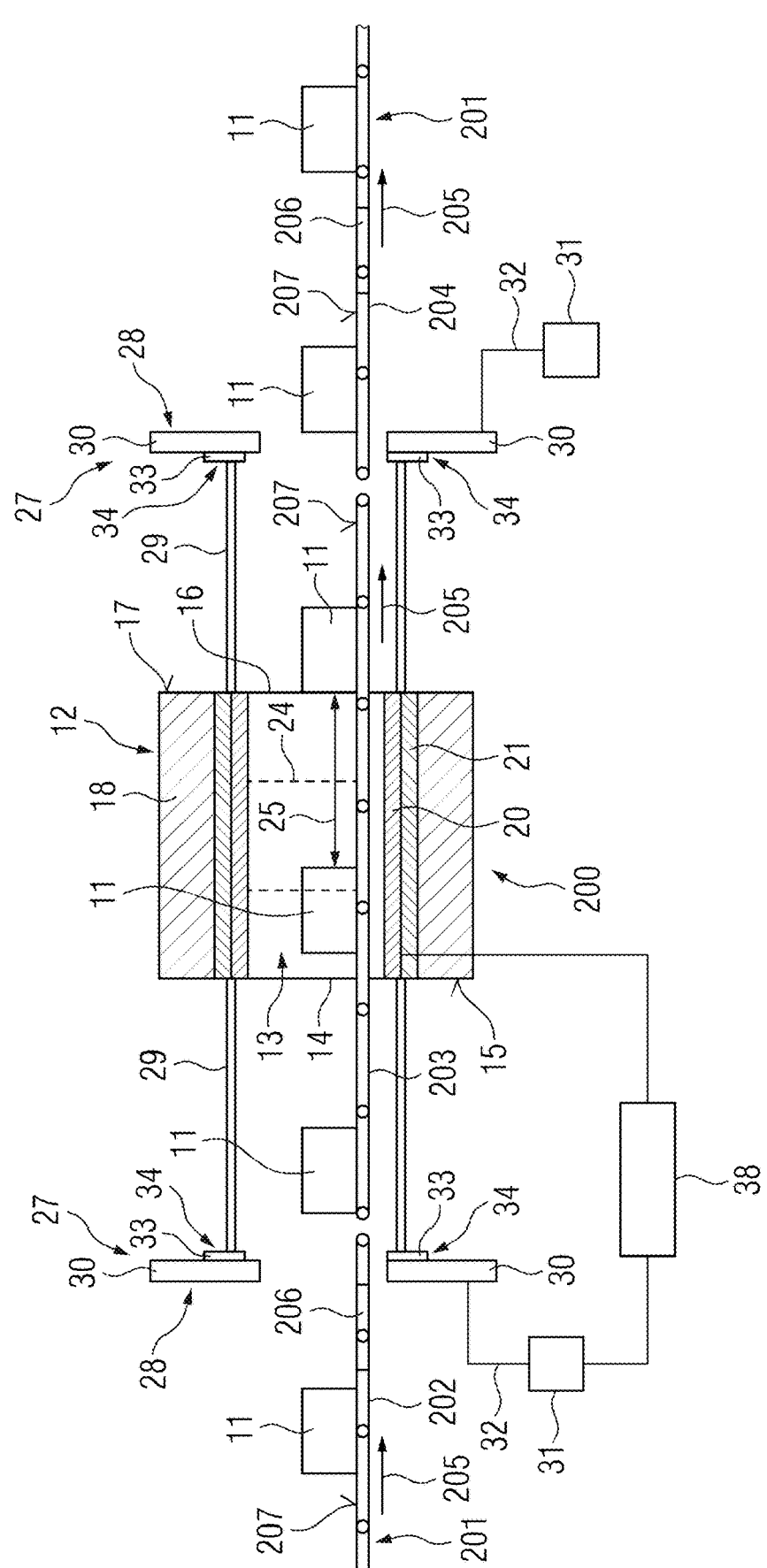
FIG. 4 illustrates a third embodiment of the example magnetic resonance apparatus with RF shielding in a diagrammatic view.

FIG. 4 shows an alternative exemplary embodiment of the magnetic resonance apparatus 200. Components, features and functions that essentially remain the same are denoted by the same reference characters among FIGS. 1-4. The following description is essentially limited to the differences from the exemplary embodiments in FIGS. 1 to 3, reference being made to the description of the exemplary embodiments in FIGS. 1 to 3 with regard to components, features, and functions that remain the same.

The magnetic resonance apparatus 100 in FIG. 4 has a transport apparatus 201 comprising three conveyor belts 202, 203, 204. The three conveyor belts 202, 203, 204 are arranged one after the other in the direction of transport 205. A first conveyor belt 202 extends in the direction of transport 205 until shortly after the first door unit 28. A second conveyor belt 203 extends in the direction of transport 205 from the first conveyor belt 202, e.g. from the end of the first conveyor belt 202 pointing in the direction of transport 205 to shortly before the second door unit 28. A third conveyor belt 204 extends from shortly before the second door unit 28 away in the direction of transport 205.

The first conveyor belt 202 and the third conveyor belt 204 have an RF shielding material. In an embodiment, the first conveyor belt 202 and the third conveyor belt 204 each have segments 206 with an RF shielding material. For example, these segments 206 may be arranged at uniform intervals in the two conveyor belts 202, 204 and in between, in each case, a storage area 207 for storage and/or positioning of samples 11.

When the two door units 28, e.g. the first flaps 30 with the second flap 30, the RF shielding material, e.g. the segments 206 with the RF shielding material, form a contact area between the two flaps 30. In an embodiment, the two flaps 30 of the respective door unit 28 have a smooth, non-toothed edge area, which comes into contact with the first or the third conveyor belt 202, 204 when the door unit 28 is closed, and thus creates an electrically conductive contact between the two flaps 30.

The second conveyor belt 203, on the other hand, has no RF shielding material to prevent unwanted attraction by the base magnet 18 of the magnet unit 12 and/or the generation of eddy currents.

An embodiment and arrangement of the magnet unit 12 corresponds to the embodiments relating to FIG. 1, to which reference is hereby made. An embodiment and arrangement of the cylindrical spacing elements 29 corresponds to the embodiments relating to FIG. 1, to which reference is also hereby made. In addition, an embodiment and arrangement of the door units 28 corresponds to the embodiments relating to FIG. 1, to which reference is hereby made.

The magnetic resonance apparatuses 10, 100, 200 shown in FIGS. 1 to 4 may of course comprise further or alternate components that are typically associated with magnetic resonance apparatuses 10, 100, 200. A general mode of operation of a magnetic resonance apparatus 10, 100, 200 is also known to a person skilled in the art, thus dispensing with the need for a more detailed description of such components.

Although the disclosure has been illustrated and described in more detail by the preferred exemplary embodiment, the disclosure is not limited by the disclosed examples and other variations may be derived therefrom by a person skilled in the art without departing from the scope of the disclosure.

Independent of the grammatical term usage, individuals with male, female or other gender identities are included within the term.

The various components described herein may be referred to as "units" or "modules." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein.

Such components may be configured to operate independently, or configured to execute instructions or computer programs that are stored on a suitable computer-readable medium. Regardless of the particular implementation, such units modules, as applicable and relevant, may alternatively be referred to herein as "assemblies," "circuitry," "controllers," "processors," or "processing circuitry," or alternatively as noted herein.

What is claimed is:

1. A magnetic resonance apparatus for detecting a property of a sample, comprising:
    a magnet assembly comprising a base magnet and a radio frequency (RF) antenna assembly;
    a sample receiving area at least partially surrounded by the magnet assembly;
    a transport apparatus comprising a conveyor belt including a recess, the transport apparatus being configured to introduce the sample into the sample receiving area; and
    an RF shielding assembly comprising a door assembly including a first flap having a first RF seal and a second flap having a second RF seal, the RF shielding assembly being configured to shield the sample receiving area from a region external to the magnetic resonance apparatus via the first RF seal of the first flap and the second RF seal of the second flap engaging with the recess of the conveyor belt to provide RF shielding.

2. The magnetic resonance apparatus as claimed in claim 1, wherein the sample comprises a foodstuff.

3. The magnetic resonance apparatus as claimed in claim 1,
    wherein the sample receiving area is surrounded cylindrically by the magnet assembly and comprises an inlet opening and an outlet opening, and
    wherein the RF shielding assembly is arranged around the inlet opening and/or around the outlet opening.

4. The magnetic resonance apparatus as claimed in claim 1, wherein in the RF shielding assembly is arranged outside the sample receiving area.

5. The magnetic resonance apparatus as claimed in claim 1,
    wherein the sample receiving area is configured to be closed or opened via the door assembly.

6. The magnetic resonance apparatus as claimed in claim 1, wherein the RF shielding assembly further comprises one or more cylindrical spacing elements arranged on a front side and/or on a rear side of the magnet assembly, and
    wherein the one or more cylindrical spacing elements are arranged between the sample receiving area and the door assembly.

7. The magnetic resonance apparatus as claimed in claim 6, wherein the one or more cylindrical spacing elements are arranged in an RF-sealing manner on the front side and/or on the rear side of the magnet assembly.

8. The magnetic resonance apparatus as claimed in claim 1, wherein:
    the RF shielding assembly comprises an electric drive assembly and/or a pneumatic drive assembly, and
    a drive torque for a movement of the first flap and the second flap of the door assembly is generated via the electric drive assembly and/or the pneumatic drive assembly.

9. The magnetic resonance apparatus as claimed in claim 8, wherein the RF shielding assembly further comprises a transmission element configured to transmit a drive torque generated by the electric drive assembly and/or the pneumatic drive assembly to the first flap and the second flap of the door assembly.

10. The magnetic resonance apparatus as claimed in claim 1, wherein the door assembly comprises one or more further RF seals arranged between the first flap and the one or more cylindrical spacing elements, and/or between iii) the second flap and the one or more cylindrical spacing elements.

11. The magnetic resonance apparatus as claimed in claim 1, wherein the first flap and/or the second flap are arranged in a closed state of the door assembly within the recess of the conveyor belt.

12. The magnetic resonance apparatus as claimed in claim 1, wherein:

the recess of the conveyor belt is from among a plurality of recesses that are arranged in a transverse direction of the conveyor belt in a line one after the other, the first flap comprises a first tooth system in a contact area with the second flap, the second flap comprises a second tooth system corresponding to the first flap in the contact area with the first flap, and in a closed state of the door assembly, the first and the second tooth systems interlock via the plurality of recesses of the conveyor belt.

13. The magnetic resonance apparatus as claimed in claim 1, wherein the recess of the conveyor belt is from among a plurality of recesses arranged in a longitudinal direction that extends in a direction of transport of the conveyor belt.

14. The magnetic resonance apparatus as claimed in claim 1 further comprising:

a controller configured to automatically control a movement of the transport apparatus and/or a closing of the door assembly based upon magnetic resonance measurements of successive ones of the samples.

15. A magnetic resonance apparatus for detecting a property of a sample, comprising:

a magnet assembly comprising a base magnet and a radio frequency (RF) antenna assembly;

a sample receiving area at least partially surrounded by the magnet assembly;

a transport apparatus configured to introduce the sample into the sample receiving area, the transport apparatus comprising:

at least two conveyor belts that are arranged one after the other in a direction of transport; and a transition area disposed between the at least two conveyor belts; and an RF shielding assembly comprising a door assembly, the RF shielding assembly being configured to shield the sample receiving area from a region external to the magnetic resonance apparatus, wherein the sample receiving area is configured to be closed or opened via the door assembly, and wherein the door assembly is arranged in a closed state of the door assembly in the transition area.

16. A magnetic resonance apparatus for detecting a property of a sample, comprising:

a magnet assembly comprising a base magnet and a radio frequency (RF) antenna assembly;

a sample receiving area at least partially surrounded by the magnet assembly;

a transport apparatus configured to introduce the sample into the sample receiving area; and an RF shielding assembly configured to shield the sample receiving area from a region external to the magnetic resonance apparatus, wherein the transport apparatus comprises at least one conveyor belt comprising an RF shielding material.

* * * * *